United States Patent [19]

McRae

[11] Plant 4,969

[45] Dec. 28, 1982

[54] LILY PLANT: LILIUM GOLDDIGGER

[75] Inventor: Edward A. McRae, Boring, Oreg.

[73] Assignee: Melridge, Inc., Sandy, Oreg.

[21] Appl. No.: 258,742

[22] Filed: Apr. 29, 1981

[30] Foreign Application Priority Data

May 29, 1980 [NL] Netherlands ..... LEL 99

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of large flowers of excellent form, unusual color, and long persistence, both on the plant and as cut flowers. The plant is characterized by an improved capability of being forced into flower under glass, increased resistance to leaf scorch and bud abortion, improved inflorescence, buds of an intense yellow color, and flowers which also are of an intense yellow color and characterized further by the presence of relatively thick, broad, and overlapping tepals lightly spotted with tiny pigmented papillae.

1 Drawing Figure

BACKGROUND AND GENERAL STATEMENT OF THE INVENTION

My new variety of lily plant is classified botanically as a Lilium hybrid; commercially, as an upright Asiatic hybrid, Division I-A in the Horticultural Classification of the Genus Lilium adopted by The Royal Horticultural Society of London.

My new variety of lily plant originated as a seedling selected from a group of seedlings among the seedling beds of test crosses at Oregon Bulb Farms, Sandy, Oreg. The cross was made in 1969. The lily plant first flowered in 1971.

The cross was made during a breeding program having as its objective the production of brilliantly-colored, upright-flowering lily cultivars, which would perform well when forced into flower under glass throughout the year, in addition to meeting the requirements of vigor, disease resistance, and rapid natural propagation and field growth. Cultivars were sought which would be disease resistant, virus tolerant, and not susceptible to scorch and bud abortion when forced under glass.

The cross was made between the seed parent Lilium 'Joan Evans' (unpatented) and the pollen parent Lilium 'Connecticut King' (unpatented).

My new lily plant is characterized by rapid natural propagation under field conditions and by vigorous and healthy growth when forced under glass with improved resistance to leaf scorch and bud abortion. It is further characterized by improved inflorescence, buds of an intense yellow color, and flowers which are also of an intense yellow color. The flowers have relatively thick, broad and overlapping tepals lightly spotted with tiny, pigmented papillae.

Lilium 'Golddigger' most closely resembles the older cultivar 'Connecticut King' which is its pollen parent. However, it differs from it and is superior to it, in its intensely yellow bud color, its intensely yellow flower color, and the presence of broader and overlapping lightly spotted tepals. It also can be forced into flower under glass more rapidly than can 'Connecticut King' and it demonstrates improved resistance to leaf scorch and bud abortion upon forcing.

My new variety of lily plant has been asexually produced by me and under my direction at Oregon Bulb Farms in Sandy, Oreg. Successive generations produced by bulb scale propagation and natural propagation from below ground stem bulblets have demonstrated that the novel and distinctive characteristics of my new variety are fixed and hold true under asexually propagation from generation to generation.

THE DRAWING

My new variety of lily plant is illustrated on the accompanying photographic rendering which shows the plant, its foliage, its buds in their various stages of development, and the open bloom in full color.

DESCRIPTION OF THE NEW VARIETY

The following is a detailed description of my new variety of Asiatic hybrid lily with nomenclature according to the *International Lily Register* (The Royal Horticultural Society, London, Second Edition, (1969)) and with color designations according to The Royal Horticultural Society Colour Chart, published by The Royal Horticultural Society in 1966.

THE PLANT

Form: Bulbous monocotyledon.

Height:

*Bulbs.*—12–15 cm in circumference produce stems 60–70 cm tall (24–28") on the average, with adequate light levels.

*Plants.*—Grown in the field in their second season after scaling produce stems about 60–80 cm (24–32") tall.

Growth: Vigorous, with considerable strength.

Foliage: Abundant, about 80–100 leaves per stem.

*Size of leaves.*—Short and broad; average 5–6 cm (2–2½") long and 1 cm (⅜") wide.

*Shape of leaves.*—Lanceolate.

*Texture of leaves.*—Leaves entire (not serrated), smooth and glossy.

Color of leaves, upperside: Medium to deep green.

Color of leaves, underside: Medium green.

Ribs and veins of leaves: Typical monocotyledonous venation; light green parallel veins.

INFLORESCENCE

Compact raceme with no secondary buds. Bulbs 12–15 cm in circumference produce an average of 5–8 buds; buds show their rich yellow color well before the flowers open.

Peduncle and pedicel: Glabrous.
Strength of infloresence: Strong; does not require staking, when plants receive adequate light.
Color of inflorescence: Medium green, sometimes with a light reddish-purple overlay.

THE BUDS

Size: 7–9 cm (3–3½″) long, 2–4 cm (¾–1″) wide.
Form: Lanceolate with obtuse tip; typical of Asiatic hybrid lilies.
Opening characteristics:
*Opens slowly.*—Opens in about one hour in response to morning light; flowers farther up the stem open on subsequent days over an interval of 1–2 weeks. Typical of Asiatic hybrid lilies.
Color of mature buds: Brilliant yellow (R.H.S. Colour Chart #9A).

THE FLOWER

Blooms: Late June or early July in Western Oregon, in midseason, once, and profusely.
Flower size: Flower diameter is 14–17 cm (5½–7″).
*Inner tepals.*—Are 4.0–4.5 cm (1½–1¾″) wide.
*Outer tepals.*—Are 2.5–3.0 cm (1–1¼″) wide.
*Shape when flower first opens.*—Shallow bowl-shape with slightly recurved tepal tips. Tepals recurve more as flower ages.
Tepal arrangement: Typical of the genus Lilium, with 6 entire, imbricated tepals.
Color, outer tepal: Brilliant yellow (The Royal Horticultural Society of London's Color Code #9A.
Color, base of tepals: Gold (R.H.S. Colour Chart #14A) flush 2–3 cm wide and deep shades into brilliant yellow (R.H.S. Colour Chart #9A).
Color, inside tepals: Brilliant yellow (R.H.S. Colour Chart #9A).
Color, reverse of tepal: Brilliant yellow (R.H.S. Colour Chart #9A-B).
Tepal duration: Tepals remain on individual flower for 5–7 days: stem has flowers with tepals adhering for about 3 weeks.
Flower texture: Shiny, velvety.
Persistence: Not affected by hot or wet weather; do not hang on and dry; tepals fall as flower ages.
Pedicel:
*Length.*—4–7 cm (1¾–3″); very short.
*Color.*—Medium green. Pedicel is sturdy and upright.
Disease resistance: Resistant to Botrytis blight and Fusarium bulb rot.
Fragrance: None.
Lasting quality:
*Flowers remain on plants.*—For about three to four weeks.
*Flowers remain on cut flower stems.*—For about three weeks, with adequate light levels.

REPRODUCTIVE ORGANS

Stamens and anthers: Typical of genus Lilium; six versatile anthers hang (singly) from 6 narrow filaments.
Filaments: 5–6 cm (2″) long and light yellow.
Pollen: Golden brown.
Pistil: 1, typical of genus Lilium; style is 5–6 cm (2″) long.
Stigma: Small, three-lobed, purple-brown.
Ovary: Typical of genus Lilium; superior, single, 6-chambered ovary.

THE FRUIT

Fruit: Fertile, an ovoid to oblong capsule with 6 chambers.
Color at maturity: Medium green, sometimes lightly overlaid with soft purple; fades to soft brown when fruit splits open to release seeds.

THE BULBS

Color of bulbs: White.
Size of bulbs: Usual commercial size is 12–20 cm (5–8″) in circumference; bulbs can reach much larger size if this is desired.

I claim:

1. The new and distinctive variety of Asiatic hybrid lily plant substantially as herein shown and described, characterized by improved capability of being forced into flower under glass, increased resistance to leaf scorch and bud abortion when forced into flower under glass, improved inflorescence, buds of intense yellow color, and flowers which are also of an intense yellow color and characterized further by the presence of relatively thick, broad and overlapping tepals lightly spotted with tiny, pigmented papillae.

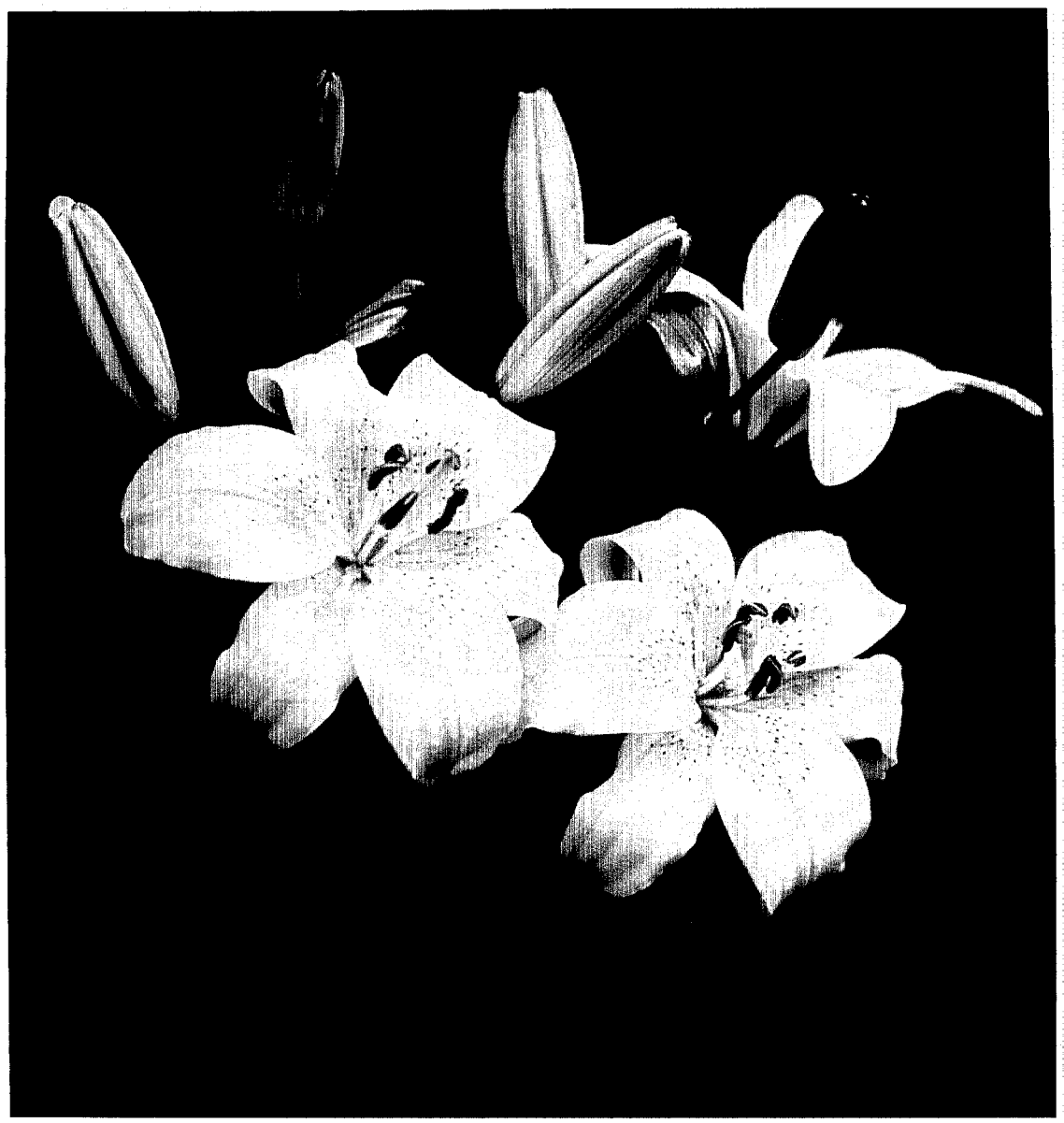

* * * * *